United States Patent
Shieh

Patent Number: 5,945,641
Date of Patent: Aug. 31, 1999

[54] STETHOSCOPE STRUCTURE

[76] Inventor: Woei-Kang Shieh, 4F, No. 63, HwaLin Street ShihLin, Taipei City, Taiwan

[21] Appl. No.: 09/119,250

[22] Filed: Jul. 20, 1998

[51] Int. Cl.$^6$ ........................................ A61B 7/02
[52] U.S. Cl. ........................................ 181/131; 181/137
[58] Field of Search ................................. 181/131, 137; 381/34

[56] References Cited

U.S. PATENT DOCUMENTS

| | | | |
|---|---|---|---|
| 4,997,055 | 3/1991 | Grady | 181/131 |
| 5,747,752 | 5/1998 | Selinger | 181/131 |
| 5,798,489 | 8/1998 | Gillio | 181/131 |

Primary Examiner—Khanh Dang

[57] ABSTRACT

A stethoscope includes a tubing having a first end to which an adapter is releasably mounted and second ends to which a pair of binaurals are mounted and a plurality of chest pieces selectively and interchangeably connected to the adapter. Each of the chest pieces has a tubular portion with a sound channel formed therein. The chest piece has formed on the tubular portion a guiding slot extending axially and a holding slot extending circumferentially and in connection with the guiding slot. The tubular portion of the chest piece has a deep recess formed on the holding slot. The adapter has a bore to receive the tubular portion of the chest piece therein. The bore has a radially extending hole within which a spherical member is movably received and biased by a spring to partially project into the bore so that in inserting the tubular portion of the chest piece into the bore, the spherical member is positioned in and guided by the guiding slot and the holding slot to reach the deep recess and be securely held therein and thus releasably securing the chest piece to the adapter.

5 Claims, 4 Drawing Sheets

STETHOSCOPE STRUCTURE

FIELD OF THE INVENTION

The present invention relates generally to a stethoscope structure and in particular to a stethoscope which comprises a plurality of chest pieces that are selectively and interchangeably mounted to the tubing of the stethoscope by means of an adapter.

BACKGROUND OF THE INVENTION

A stethoscope is an important tool for medical doctors to perform diagnosis of patients. Conventionally, a stethoscope comprises a single chest piece which is usually to be placed on the body of the patient, such as chest or stomach, to receive vibration signals therefrom and a pair of binaurals having ear tips to be inserted into the ears of the doctor to supply the vibration signals to the doctor. A tubing, usually made of rubber or similar material, is connected between the chest piece and the binaurals for transmission of the vibration of the patient's body to the ear tips.

However, since there are different vibration signals of different frequencies generated inside the human body and different signals provide different information to the doctor, in doing diagnosis, the doctor may have to switch between two or more different stethoscopes for picking up signals of different frequencies. This is quite cumbersome to the doctor.

To overcome such a problem, a stethoscope having a turret on which two or more chest pieces are mounted has been developed, as shown in FIG. 4 in which the tubing 10 has a turret type adapter 12 fixed to an end thereof with two chest pieces 14 mounted on the turret 12. Such a multiple chest piece stethoscope allows the doctor to switch between the chest pieces by rotating the turret 12. Such a device has a disadvantage that mechanical wearing usually occur in the turret after a long term service of the stethoscope.

Furthermore, those conventional stethoscopes are the so-called "fixed" design which needs to be periodically disassembled for maintenance and cleaning purpose and the disassembling operation may need hand tools. This is, to some extent, inconvenient and troublesome to the doctors.

Thus, it is desirable to provide a stethoscope structure which allows the medical doctors to swiftly switch between different chest pieces and provides easy maintenance and cleaning so as to overcome the drawbacks of the prior art designs.

SUMMARY OF THE INVENTION

Therefor, an object of the present invention is to provide a stethoscope comprising a plurality of chest pieces which are selectively and interchangeably connected to the tubing of the stethoscope by means of an adapter so as to allow a user to efficiently change different chest pieces for obtaining different diagnosis information.

Another object of the present invention is to provide a stethoscope structure having a plurality of chest pieces in which the chest pieces are easily dismounted from the tubing to facilitate the maintenance and cleaning of the stethoscope.

A further object of the present invention is to provide a stethoscope structure which allows a user to change only a portion of the stethoscope when the portion is broken so as to reduce the cost of fixing or purchasing the stethoscope.

To achieve the above objects, in accordance with the present invention, there is provided a stethoscope comprising a tubing having a first end to which an adapter is releasably mounted and second ends to which a pair of binaurals are mounted and a plurality of chest pieces selectively and interchangeably connected to the adapter. Each of the chest pieces comprises a tubular portion with a sound channel formed therein. The chest piece has formed on the tubular portion a guiding slot extending axially and a holding slot extending circumferentially and in connection with the guiding slot. The tubular portion of the chest piece has a deep recess formed on the holding slot. The adapter has a bore to receive the tubular portion of the chest piece therein. The bore has a radially extending hole within which a spherical member is movably received and biased by a spring to partially project into the bore so that in inserting the tubular portion of the chest piece into the bore, the spherical member is positioned in and guided by the guiding slot and the holding slot to reach the deep recess so as to be securely held therein and thus releasably securing the chest piece to the adapter.

BRIEF DESCRIPTION OF THE DRAWINGS

The present invention will be better understood from the following description of a preferred embodiment thereof, with reference to the attached drawings, wherein.

DETAILED DESCRIPTION OF THE PREFERRED EMBODIMENT

Figure 1:
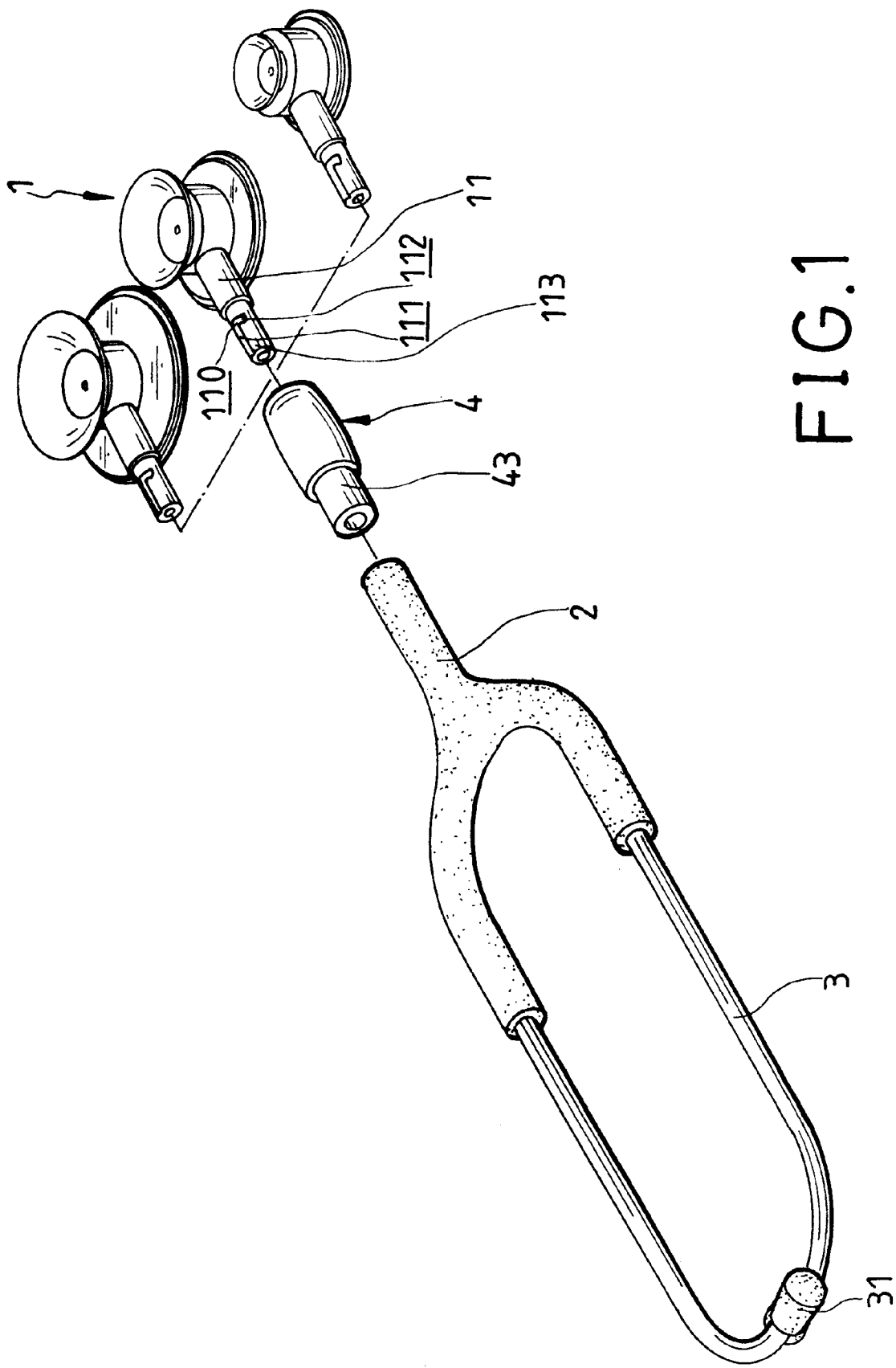
FIG. 1 is an exploded perspective view showing a stethoscope constructed in accordance with the present invention which comprises three chest pieces to be selectively and interchangeably mounted to the stethoscope.

With reference to the drawings and in particular to FIG. 1, wherein a stethoscope constructed in accordance with the present invention is shown, the stethoscope of the present invention comprises a tubing 2 having a first end to which an adapter 4 is removably connected and second ends to which a pair of binaurals 3 are mounted, each having an ear tip 31 adapted to be inserted into the ears of a user, and a plurality of chest pieces 1 which are selectively and interchangeably connected to the adapter 4 in a releasable and quick engaging manner to be described hereinafter so that the user of the stethoscope of the present invention may quickly switch between different ones of the chest pieces 1.

Although only three chest pieces 1 are shown in the drawings, it is understood that, if desired, there may be more than or less than three such chest pieces included in the stethoscope structure of the present invention.

Figure 2:
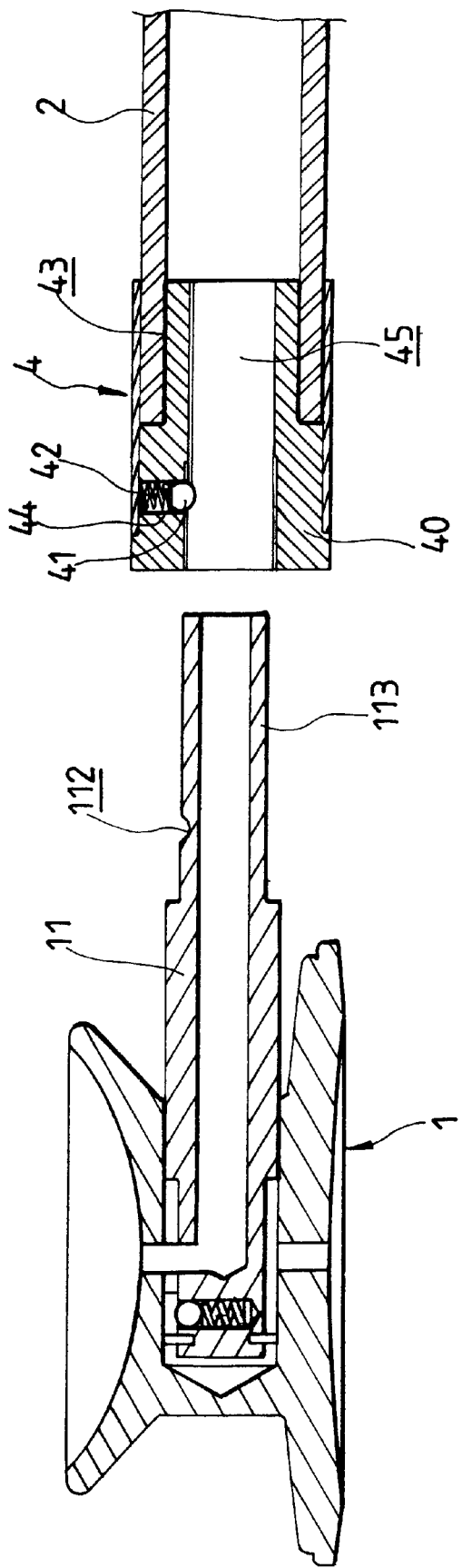
FIG. 2 is a cross-sectional view of a portion of the stethoscope of the present invention in which one of the chest pieces is to be connected to the tubing of the stethoscope by means of an adapter.
Figure 3:
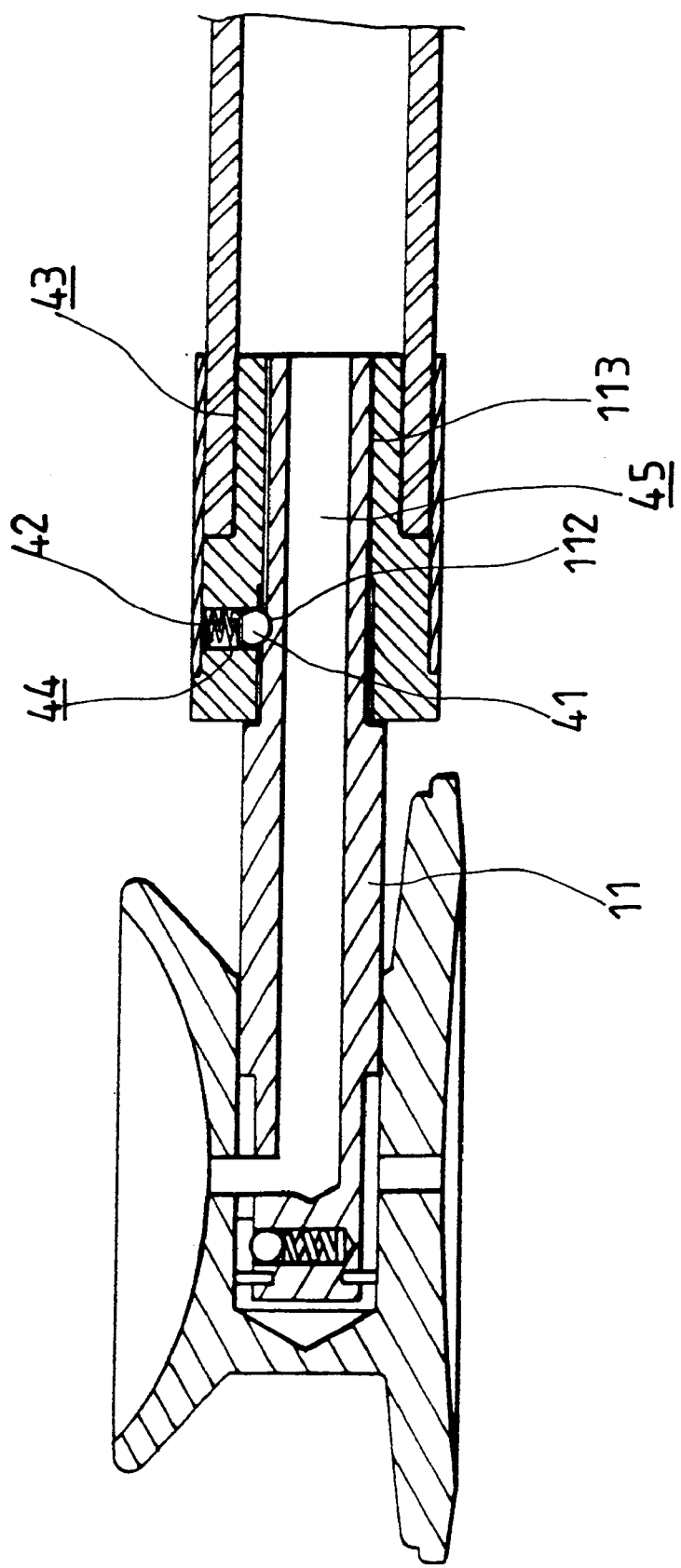
FIG. 3 is a cross-sectional view of a portion of the stethoscope of the present invention in which the chest piece is connected to the tubing by means of the adapter.
Figure 4:
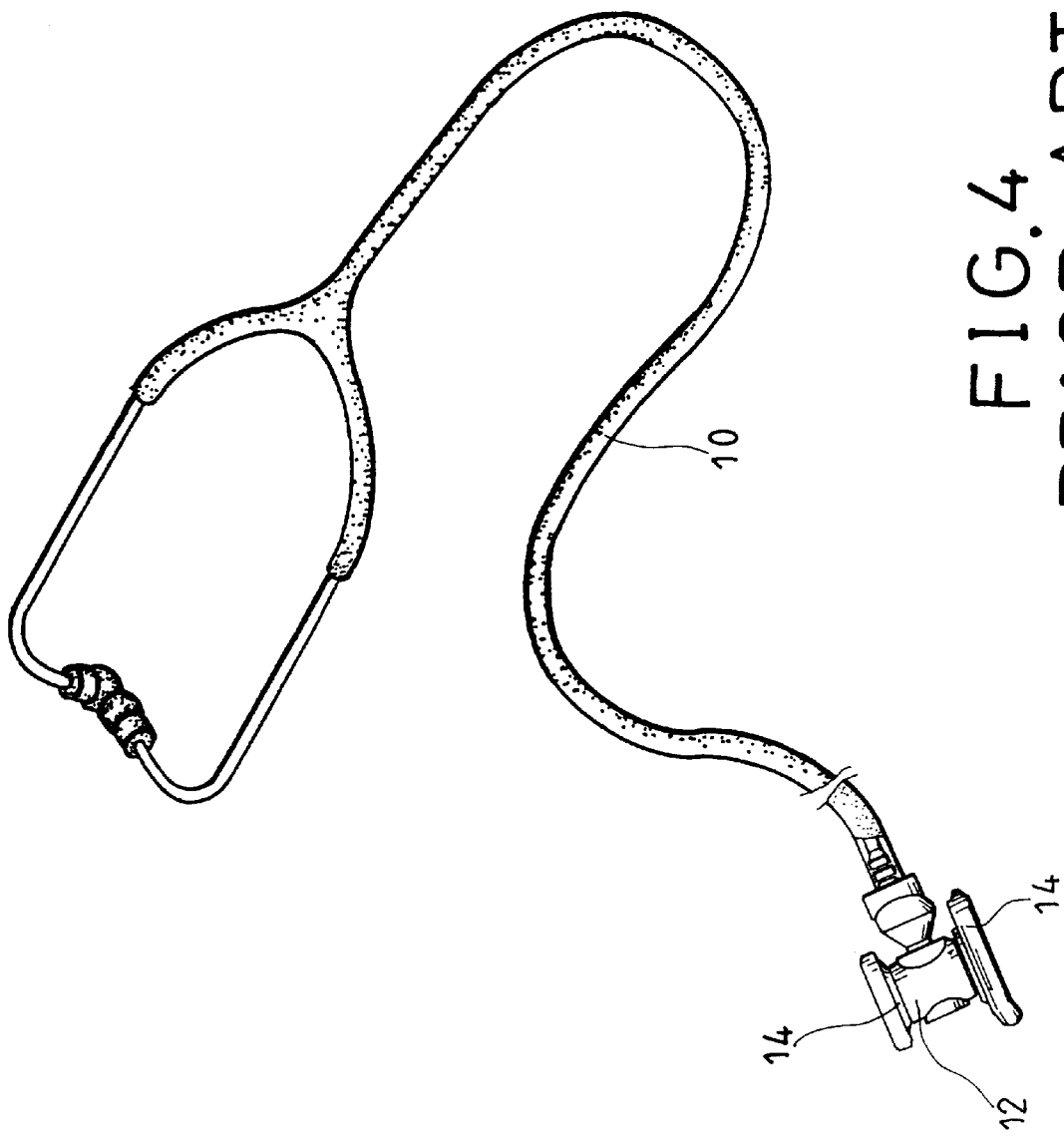
FIG. 4 is a perspective view showing a turret type stethoscope in accordance with the prior art design.

Further referring to FIGS. 2 and 3, each of the chest pieces 1 has a sound channel 11 in the form of a tube having a tubular end section 113 extending in an axial direction and sized to fit into a bore 45 of the adapter 4. The tubular portion 113 of the sound channel 11 of the chest piece 1 comprises a guiding slot 111 (FIG. 1) extending in the axial direction and a holding slot 110 in connection with the guiding slot 111 and extending in a circumferential direction and preferably substantially normal to the guiding slot 111.

The holding slot 110 is provided with a deeply recessed end 112 having a depth greater than the holding slot 110.

The adapter 4 that comprises the bore 45 has a circumferential receiving recess 43 sized to tightly receive the first end of the tubing 2 therein so as to fix the adapter 4 to the first end of the tubing 2. The adapter 4 also has a radially extending hole 44 formed on an inside surface of the bore 45 within which a spherical member 41 is movably received. The spherical member 41 is biased by an elastic or resilient member, such as a spring 42, to partially protrude into the bore 45. The protrusion of the spherical member 41 is sized substantially corresponding to the recess 112 on the holding slot 110 of the tubular portion 113 of the chest piece 1 so that by inserting the tubular portion 113 of the chest piece 1 into the bore 45 of the adapter 4 with the spherical member 41 positioned in and guided by the guiding slot 111 and then rotating the chest piece 1 with respect to the adapter 4 to have the spherical member 41 moved into and securely held in the recess 112 of the holding slot 110 of the chest piece 1, a sound engagement is established between the adapter 4 and the chest piece 1, as shown in FIG. 3.

In removing the chest piece 1 out of the adapter 4, one only needs to forcibly rotate the chest piece 1 with respect to the adapter 4 to drive the spherical member 41 back into the radially extending hole 44 which allows the chest piece 1 to move relative to the adapter 4 along the holding slot 110 and then the guiding slot 111 so as to completely separate the chest piece 1 from the adapter 4. A next one of the chest pieces 1 may then be connected to the adapter 4 to allow the user to switch between different chest pieces 1.

Quite obviously, the spring-biased spherical member 41 may be provided on the tubular portion 113 of the chest piece 1, while the guiding slot 111 and the holding slot 110 and the recess 112 for holding the spherical member 41 are formed on the inside surface of the bore 45 of the adapter 4. This is as effective in releasably mounting the chest piece 1 to the adapter 4 as the embodiment illustrated in the drawings.

Although the preferred embodiment has been described to illustrate the present invention, it is apparent that changes and modifications in the specifically described embodiments can be carried out without departing from the scope of the present invention which is intended to be limited only by the appended claims.

What is claimed is:

1. A stethoscope structure comprising a tubing having a first end to which an adapter is releasably mounted and second ends to which a pair of binaurals are mounted and at least one chest piece, the adapter comprising a bore extending in axial direction to receive a tubular portion of the chest piece inserted therein, and releasable securing means being provided to releasably secure the tubular portion of the chest piece to the bore of the adapter, the securing means comprising a securing member provided on one of the tubular portion of the chest piece and the bore of the adapter to be releasably received and held in a recess formed on a second one of the tubular portion of the chest piece and the bore of the adapter, the securing member being spring biased to be securely held within the recess so as to have the chest piece securely fixed to the adapter; wherein the securing member comprises a spherical member which is received within a radially extending hole formed on inside surface of the bore of the adapter and is biased to partially protrude into the bore and wherein the tubular portion of the chest piece comprises a slot for receiving and guiding the spherical member in inserting the tubular portion into the bore, the recess being formed in the slot to receive and hold the spherical member.

2. The stethoscope as claimed in claim 1, wherein the spherical member is biased by a spring disposed within the radially extending hole.

3. The stethoscope as claimed in claim 1, further comprising a next chest piece selectively and interchangeably mounted to the adapter.

4. The stethoscope as claimed in claim 3, comprising three chest pieces to be selectively and interchangeably connected to the adapter by having the tubular portion thereof inserted into the bore of the adapter.

5. The stethoscope as claimed in claim 1, wherein the adapter comprises a circumferential receiving recess into which the first end of the tubing is tightly inserted so as to releasably mount the adapter to the tubing.

\* \* \* \* \*